United States Patent [19]

Frisch et al.

[11] Patent Number: 4,810,246
[45] Date of Patent: Mar. 7, 1989

[54] DISPOSABLE CELL CULTURE CHAMBER WITH REMOTE ACCESS

[75] Inventors: Eldon E. Frisch, Midland; Adrian Kantrowitz, Pontiac; Paul S. Freed, Bloomfield Hill, all of Mich.

[73] Assignee: L. Vad Technology, Inc., Pontiac, Mich.

[21] Appl. No.: 116,311

[22] Filed: Nov. 4, 1987

[51] Int. Cl.$^4$ ............................................. A61M 5/00
[52] U.S. Cl. ..................... 604/93; 604/175; 604/891.1
[58] Field of Search ............... 604/175, 174, 264, 905, 604/93, 8–10

[56] References Cited

U.S. PATENT DOCUMENTS 4,605,007 8/1986 Heraly ..................... 128/419 PT
4,634,422 1/1987 Kantrowitz et al. ............ 604/175 X Primary Examiner—Stephen C. Pellegrino
Attorney, Agent, or Firm—Basile and Hanlon

[57] ABSTRACT

A combination is provided of a percutaneous lead designed for implantation in the human body, which lead has a surface which is adapted to pass through and be exposed to the dermis of a patient when the device is implanted. Said surface is adapted to receive the growth of a cultured autogenous fibroblast coating on an etched, nanoporous surface. A liquid tight sealed removable, disposable chamber encloses said surface, said chamber being provided with openings for introduction therein of finely divided living dermal tissue suspended in a liquid carrier, thus providing a means for formation of the cultured surfaces which can be easily handled. The disposable chamber is removed and discarded at the time of surgery.

6 Claims, 1 Drawing Sheet

DISPOSABLE CELL CULTURE CHAMBER WITH REMOTE ACCESS

BACKGROUND OF THE INVENTION

Percutaneous access devices are employed to establish a continuous connection or pathway, generally by means of an appropriate conduit such as a catheter, through an unnatural opening through the skin of a patient to facilitate external access to the body's interior. The conduit may connect internally, for example, to an internal organ, to a prosthetic device, to a blood vessel or nerve, to muscle, tendon, or bone, or merely terminate to one of the body's cavities. The external connection may be used for a variety of purposes such as ingress of energy, fluids or drugs, removal of fluids, or for attachment of a prosthetic device to bone, muscle, or tendon. A fundamental problem confronted in the use of percutaneous access devices is that infection can frequently occur because it has not generally been possible to obtain an adequate seal between the skin and the conduit to prevent the ingress of infection-causing agents through the opening in the skin. In order to minimize this problem and to avoid other problems such as marsupialization or sinus tract formation caused by efforts of the epidermus to close the unnatural opening, it has been proposed to utilize a percutaneous access device having a peridermal component on the conduit, on the surfaces of which skin cells from the patient have been cultured and are adherent.

One manner in which the foregoing problems have been overcome or minimized is by the use of a peridermal component designed to be implanted immediately beneath the skin and having a surface provided with a cell-cultured adherent fibroblast coating. Such coating is cultured on a nanoporous surface provided on said peridermal component in accordance with the teachings of U.S. Pat. No. 4,634,422. The term "nanoporous" is intended to have the same meaning as defined in said patent.

A critical step in the formation of infection resistant cell cultured percutaneous leads is the step of growing and maintaining a viable, undamaged layer of cells from a sample of the patients skin. It has hithertofore been difficult to transport and handle the device after cell-culturing while maintaining cleanliness and sterility, and without damage to the cell layer. Hithertofore the cell culturing of the nanoporous component has been completed before assembly to the conduit component. Subsequent assembly of the cultured component is difficult because of the challenges associated with maintaining sterility or aseptic conditions while at the same time attempting to neither disturb the cultured cells nor to allow them to dry out. It has also been difficult to achieve tight, secure, and void-free bonding of the cell cultured component to the conduit component. Mechanical interlocking has hithertofore been unreliable, and the use of glues or adhesives precluded because the cell-culture nanoporous component must be kept wet, most glues or adhesives are cytotoxic, and because of the drying of the cell-culture layer during the time required for the bonding to become secure.

SUMMARY OF THE INVENTION

The present invention provides a means for culturing the cells upon a percutaneous access device after said device has been entirely preassembled, packaged and sterilized without loss of sterility and without contaminating the other components of the implantable device. The preassembled, packaged, sterilized percutaneous access devices of this invention are also capable of being shipped or transported while maintaining sterility of the entire device while the cell-cultured layer on the nonporous component remains viable and moist.

The present invention provides in combination a preassembled access device designed for percutaneous implantation in a human body, with a disposable container therefor which provides a means for remote access cell culturing thereon and for safe, sterile storage of the device until the device is implanted. The device is provided with a surface which is adapted, generally by being etched or otherwise made nanoporous, to receive the growth of a cultured autogenous fibroblast coating thereon which is formed by culturing of a suspension of finely divided dermal tissue of the patient in a liquid carrier. In accordance with the invention a removable cell-culture device is attached to the nanoporous component which is provided with openings or leads for introduction or removal of fluids, thus permitting aseptic access to the removable chamber. The chamber is disposable and can simply be cut away after opening of the sterile package and discarded at the time of surgery immediately prior to implantation of the percutaneous access device. The preferred material for formation of the chamber is a silicone elastomer but other biologically inert materials can be substituted.

DRAWINGS

For a fuller understanding of the nature and objects of the invention reference should be had to the following detailed description and drawings wherein:

FIG. 1 is a perspective view of a peridermal nanoporous component of a percutaneous access device attached to a disposable culture chamber in accordance with the invention, with parts broken away, and FIG. 2 is a cross-sectional view of such percutaneous access device and disposable culture chamber enclosed in a sterile package.

DETAILED DESCRIPTION OF THE INVENTION

Figure 1:
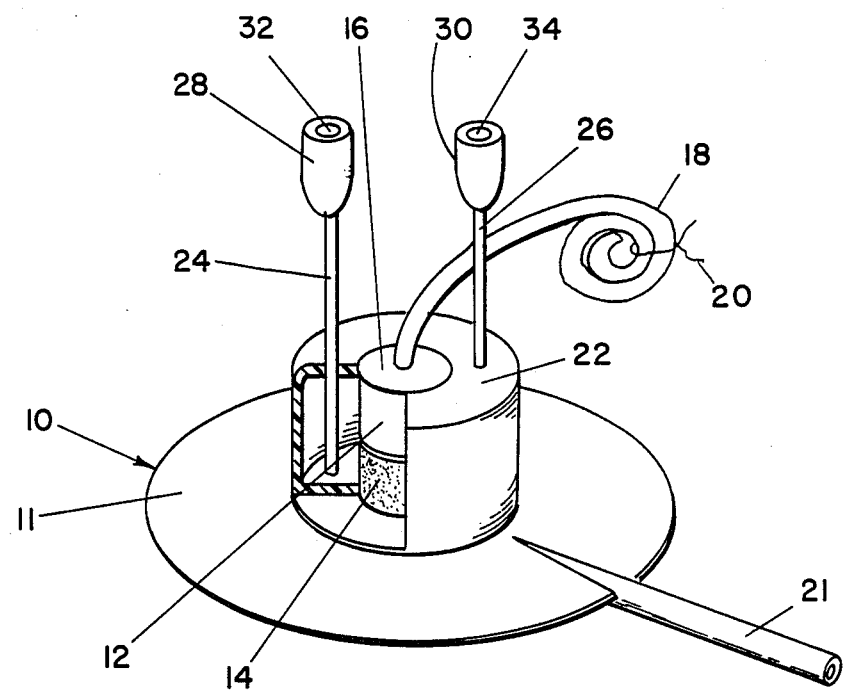

The invention is illustrated in connection with the same type of percutaneous access device as that disclosed in Freed U.S. Pat. No. 4,004,298 and Kantrowitz et al U.S. Pat. No. 4,634,422. The invention is, however, applicable to percutaneous lead devices of other types or shapes.

The peridermal component of a percutaneous access device or lead is denoted generally in the drawings by numeral 10. Component 10 includes a base portion 11, integral with and extending upwardly from which is an extension 12 adapted to be implanted immediately beneath the skin of a patient. Extension 12 is provided with a nanoporous portion 14 which is formed by etching or other means. Cells cultured from a small specimen of the patient's (or animal's) skin become adherent to the nanoporous surface and form a continuous fibroblast cell layer over the nanoporous area. Membranes of fibroblast cells in contact with the nanoporous surface form within and fill the nanopores, which typically average two nanopores per cell. When the cell-cultured peridermal component is implanted peridermally in humans or animals in a preformed fibrous tissue capsule formed by prior subdermal implantation of an identically shaped, nonporous solid implant, the cell-cultured fibroblsts on the nanoporous component become continous with the fibroblasts of the fibrous tissue capsule. As the dermis heals around the percutaneous conduit 18, the dermis also grows downward as in marsupialization until it contacts the fibroblast layer adherent to the nanoporous surface of extension 12. The dermis then joins or heals to the fibroblast layer to form a bacteriaproof seal, similar to the juncture between skin and scar, such as scar left from surgical incision. Thus the dermis becomes firmly united with the exterior surface of extension 12. Extension 12 is provided with an end closure 16, through which extends a conduit 18.

Conduit 18 may merely be a removable plug or cover to expose a connection to which an external conduit can be attached or removed as needed. Conduit 18 may also be a tube, a bundle of tubes, an insulated wire or multiple wires, or a combination of tubes and wires. Conduit 18 may incorporate a bellows capable of stretching or compression, thus permitting powering of an external prosthetic device by muscle or tendon. Conduit 18, which may be presterilized, is intended to extend outward from the patient's body to establish connection between an internal body part, cavity, or prosthetic device and something external. For packaging, conduit 18 may be tied neatly into a coil and fastened together by cord 20 or similar means. Conduit 21 may be affixed by the edge of component 10 and be in communication with a central passage in extension 12. Alternatively conduit 21 may extend centrally or otherwise through component 10 and be in communication with the central passage from extension 12. Said central passage is also in communication with conduit 18. Conduit 21 provides internal access to a body part or prosthetic device. Often the bottom of lead 10 is surfaced with a layer of inert fibrous material such as Dacron ® velour to provide a porous or textured surface into which body tissues can grow to stabilize peridermal component 10.

Around extension 12 is attached a disposable elastomeric chamber 22. Chamber 22 may be either adhered or friction fit around extension 12 to form a secure, liquidproof seal. Extending into chamber 22 are tubes 24 and 26, by means of which addition or aspiration of liquids to or from the chamber may be accomplished. Tubes 24 and 26 may be provided with enlarged ends 28 and 30 which facilitate access to the chamber 22. It will be thus appreciated that remote access to the chamber 22 is possible without contamination of the implantable device 10. Plugs or dams 32 and 34 which may also be formed of elastomeric material may be provided to provide means for closure of tubes 24 and 26 when not in use. Venting or introduction of fluids can also be accomplished simply by inserting a hypdermic needle through plugs 32 or 34. It will be thus appreciated that remote access to the chamber 22 is possible without contamination of the implantable device 10.

A dermal specimen obtained from the recipient patient is finely divided, cells are separated, grown in culture to produce fibroblasts, which when suspended in a suitable liquid medium, can thus be introduced into chamber 22 to permit an autogenous cell culture to be grown on surface 14.

Figure 2:
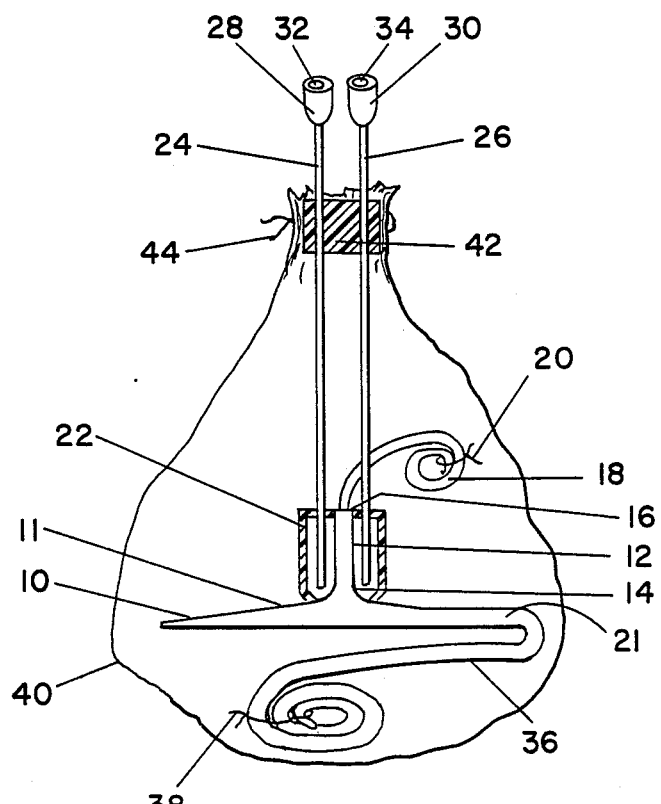

Another conduit 36 intended for implantation in the body can be extended from conduit 21. Conduit 36 may also be coiled and secured by means 38 which may be a suture or cord. Tubes 24 and 26 may optionally be extended through a suitable plug 42. A sterile plastic bag may enclose the entire above described assembly as shown in FIG. 2. Bag 40 is securely tied around plug 42 to provide a stable environment for storage and handling of the sterile assembly with the culture cells in place.

It will be readily apparent that the entire assembly can be sterilized and is of a size which will fit into a culture incubator. Optionally the entire assembly can also be packaged within a second plastic bag to avoid any possibility of contamination of the injection ports 28 and 30.

The preferred material for chamber 22 in a silicone elastomer or copolymer thereof. However, polyurethane or other elastomers may be substituted. Chamber 22 can easily be removed by cutting at the time of implantation and discarded. Chamber 22 can remain filled with liquid medium and serves to protect the cell culture layer from damage caused by any inadvertent contact during transportation or handling.

Component 10 may be formed of any suitable biocompatible material, as will be apparent to those skilled in the art. Examples of such materials are polyethylene, polyurethanes, polysulfone, silicones, and equivalent materials.

It is to be understood that the foregoing embodiments are to be considered illustrative of the invention. Various modifications, changes or alterations of the invention disclosed herein may be evident to those skilled in the art and thus the invention disclosed herein is not intended to be limited by the description hereinabove but rather is intended to be limited only by the appended claims.

What is claimed is:

1. In combination:
   A. a percutaneous access device designed for implantation in the human body, said device having a component adapted to extend through the skin to provide access from outside of the body to a subcutaneous location within the body and having a peridermal component with a surface which is adapted to be implanted immediately beneath the dermis of a patient, said surface having a porous texture and thus being adapted to receive the growth thereon of a cultured autogenous fibroblast coating thereon, and
   B. a liquid tight sealed removable, disposable chamber enclosing said surface, said chamber being provided with a remotely accessible opening for introduction therein of finely divided living dermal tissue suspended in a liquid carrier.

2. A device according to claim 1 wherein said chamber is formed of a silicone elastomer.

3. A device according to claim 1 wherein a tube is provided through said opening for addition of said dermal tissue and a second tube is provided to permit venting of said chamber.

4. A device according to claim 1 wherein said surface is nanoporous.

5. A device according to claim 1 wherein said component is a conduit attached to the top thereof adapted to extend exteriorly of the body of the patient and a conduit tube in fluid communication therewith extending from the bottom thereof which is adapted to be surgically implanted within the patients body.

6. A device according to claim 5 wherein a sterile plastic container surrounds said chamber and said catheters, said container being hermetically enclosed with the exception of an opening through which a tube connected to the opening in the chamber extends for addition of a dermal tissue suspension.

* * * * *